United States Patent [19]

Nakajima et al.

[11] Patent Number: 5,545,542

[45] Date of Patent: Aug. 13, 1996

[54] WB2663 SUBSTANCES AND METHOD FOR THEIR PRODUCTION

[75] Inventors: Hidenori Nakajima, Tsukuba; Yasuhiro Hori, Tokyo; Toshio Goto, Kobe; Shigehiro Takase, Ishioka, all of Japan; Koen Verhaeghe, Antwerp, Belgium; Hiroshi Terano, Tuchiura; Masakuni Okuhara, Tsukuba, both of Japan

[73] Assignee: Fujisawa Pharmaceutical Co., Ltd., Osaka, Japan

[21] Appl. No.: 415,160

[22] Filed: Mar. 31, 1995

Related U.S. Application Data

[63] Continuation of Ser. No. 150,207, filed as PCT/JP92/00754 Jun. 12, 1992 published as WO92/22562 Dec. 23, 1992, abandoned.

[30] Foreign Application Priority Data

Jun. 14, 1991 [JP] Japan .................................. 169104

[51] Int. Cl.$^6$ .................................................. C12P 13/00
[52] U.S. Cl. ..................... 435/128; 435/132; 435/170; 435/41; 435/822; 435/874; 424/120; 424/121
[58] Field of Search ..................................... 424/120, 121; 435/41, 128, 170, 132, 822, 874

[56] References Cited

U.S. PATENT DOCUMENTS 2,830,993  4/1958  Brossi et al. ............................ 260/287

OTHER PUBLICATIONS

Chemical Abstracts, vol. 106, No. 5, Feb 2, 1987, p. 407, AN 31372j.
Shoji et al, J of Antibiot., vol. 43, pp. 703–787, 1990.
Shoji et al, J of Antibiot. vol. 41, pp. 589–594, 1988.
The Merck Index, 1983, p. 693.

Primary Examiner—Irene Marx
Attorney, Agent, or Firm—Oblon, Spivak, McClelland, Maier & Neustadt, P.C.

[57] ABSTRACT

WB2663 substance-producing bacteria belonging to the genus Pseudomonas are cultured to produce a physiologically active substance, from which are isolated neutral substances WB2663A, WB2663B and WB2663C having respective specific rotations $[\alpha]_D^{23}$: −36° (C=0.5, CH$_2$Cl$_2$), $[\alpha]_D^{23}$: −12° (C=0.5, CH$_2$Cl$_2$), $[\alpha]_D^{23}$: −9° (C=0.5, CH$_2$Cl$_2$), These substances have an excellent antitumor effect.

4 Claims, 6 Drawing Sheets

WB2663 SUBSTANCES AND METHOD FOR THEIR PRODUCTION

This application is a continuation of application Ser. No. 08/150,207, filed on Mar. 31, 1994, abandoned which was filed as International application No. PCT/JP92/00754, on Jun. 12, 1992.

FIELD OF THE INVENTION

The present invention relates to WB2663 substances, a method for their production, and use thereof. WB2663 substances are novel substances hitherto unknown, which were separated and collected from a culture of Pseudomonas cells and which exhibit an excellent antitumor effect and are particularly useful as prophylactic and/or treatment agent for various types of tumors.

DESCRIPTION OF THE PRIOR ART

In the past, various types of antitumor agents have been developed from naturally occurring substances by methods of extraction, fermentation and chemical synthesis, etc., but as few of these exhibit a strong antitumor effect without harmful side effects, it has been earnestly desired to develop more excellent antitumor agents.

Problem to be Solved by the Invention

The present invention was undertaken in light of the above mentioned state of the current technology, with the object of developing an excellent antitumor agent which is highly safe and has a wide-ranging and powerful antitumor effect.

Means to Solve the Problem

The present invention was undertaken in order to achieve the above mentioned object.

We the present inventors focused on natural substances for the sake of safety, finally concentrating our attention on microbial fermentates, and upon investigation of various microorganisms we discovered that microorganism No. 2663 strain newly separated from soil taken in Mie Prefecture accumulates the substance of interest in a culture solution. Furthermore, upon more detailed research regarding the physicochemical properties of the substance, we discovered that it is not a single substance but rather a mixture of a number of different substances, and we succeeded in isolating 3 of these substances. These substances were confirmed to be novel substances unknown to the prior art, and were collectively named WB2663 substances, and respectively WB2663A substance, WB2663B substance and WB2663C substance. Further research resulted in the establishment of a method for their industrial production, and the present invention was thus completed.

Figure 1:
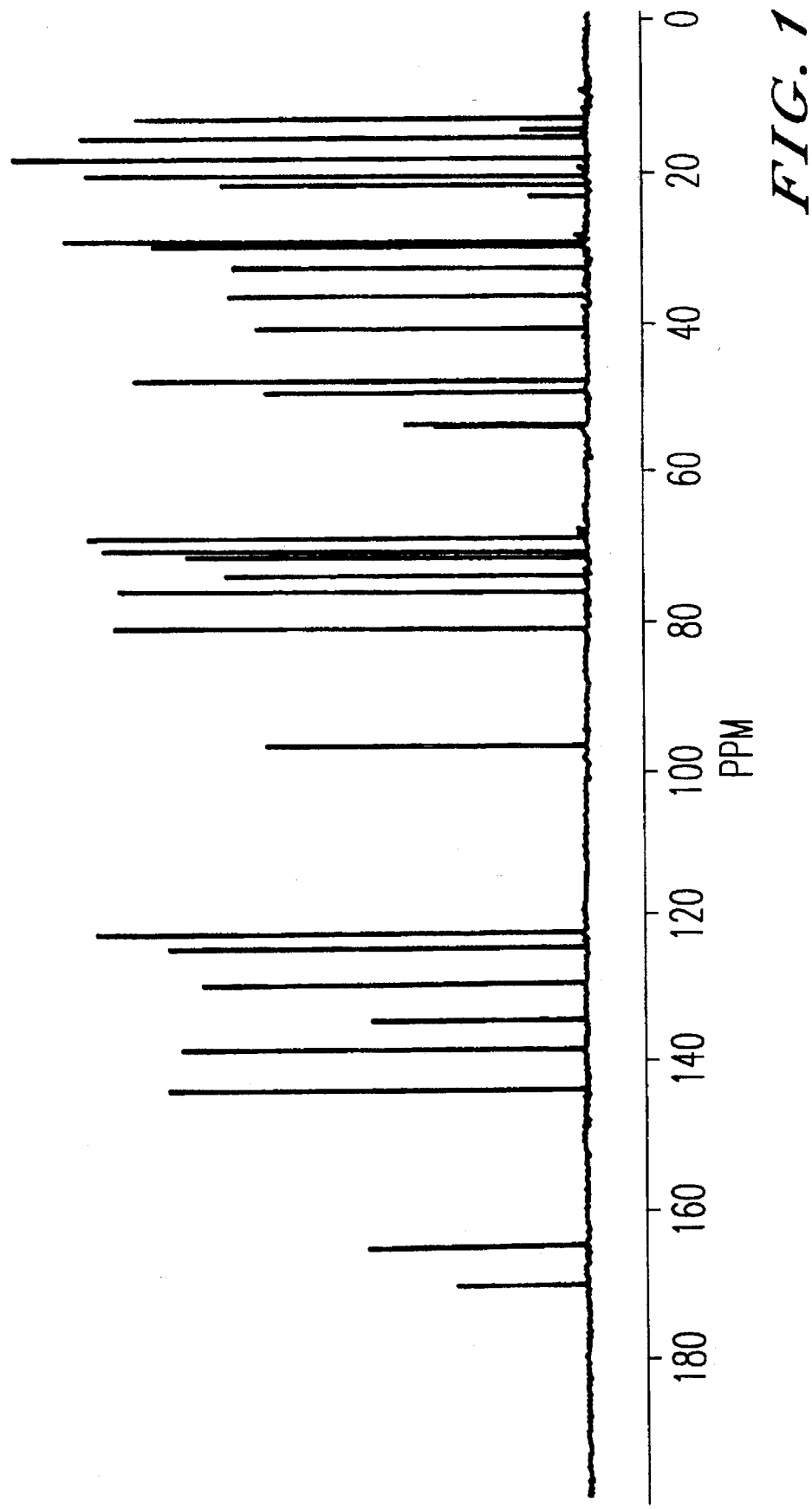
FIG. 1 is a drawing showing a $^{13}C$ nuclear magnetic resonance spectrum of WB2663A substance.

WB2663A substance, WB2663B substance and WB2663C substance according to the present invention each possess the physicochemical properties listed below.

Physicochemical Properties of WB2663A Substance (1) Color and form of substance

White needle-shaped crystals (2) Melting point

102°–104° C.

(3) Specific rotation $[\alpha]_D^{23}$: −36° (C=0.5, $CH_2Cl_2$)

(4) Molecular formula $C_{27}H_{42}ClNO_8$ (5) Elemental analysis

Calculated for $C_{27}H_{42}ClNO_8$ (%): C, 59.60; H, 7.78; N, 2.57; Cl, 6.52

Found (%): C, 60.11; H, 8.10; N, 2.44; Cl, 6.86

(6) Solubility in solvents

Readily soluble: dichloromethane, chloroform, acetone, ethyl acetate

Insoluble: hexane, water (7) Color reaction

Positive: iodine vapor reaction, cerium sulfate reaction, potassium permanganate reaction Negative: ferric chloride reaction, Ehrlich reaction, ninhydrin reaction (8) Thin-layer chromatography

| Stationary phase | Developing solvent | Rf value |
| --- | --- | --- |
| Silica gel (Silica Gel 60 $F_{254}$) (product of E. Merck Co.) | dichloromethane:methanol (20:1) | 0.47 |
| | dichloromethane:acetone (2:3) | 0.74 |

(9) Infrared absorption spectrum $\nu_{max}^{KBr}$: 3400, 2980, 2940, 1735, 1665, 1630, 1530, 1370, 1240, 1055 $cm^{-1}$

(10) High performance liquid chromatography

Column: YMCAM-303 [S-5, 120A, ODS, 4.6 mmID×250 mm; product of Yamamura Chemical Laboratories, Ltd.]

Detection: 210 nm

Developing solvent: 70% aqueous solution of methanol

Flow rate: 1 ml/min

Retention time (RT): 7.9 min

(11) $^{13}C$ nuclear magnetic resonance spectrum (100 MHz, $CD_2Cl_2$)

Chart shown in FIG. 1

$\delta_c$: 170.8(s), 165.4(s), 144.1(d), 138.7(d), 134.9(s), 129.9(d), 124.8(d), 122.7(d), 96.8(s), 81.3(d), 76.3(d), 74.0(s), 71.4(d), 70.7(d), 68.9(d), 49.2(t), 47.7(d), 40.7(t), 36.2(t), 32.4(t), 29.6(d), 29.1(q), 21.4(q), 20.2(q), 18.0(q), 15.3(q), 12.8(q).

(12) $^1H$ nuclear magnetic resonance spectrum (400 MHz, $CD_2Cl_2$)

Figure 2:
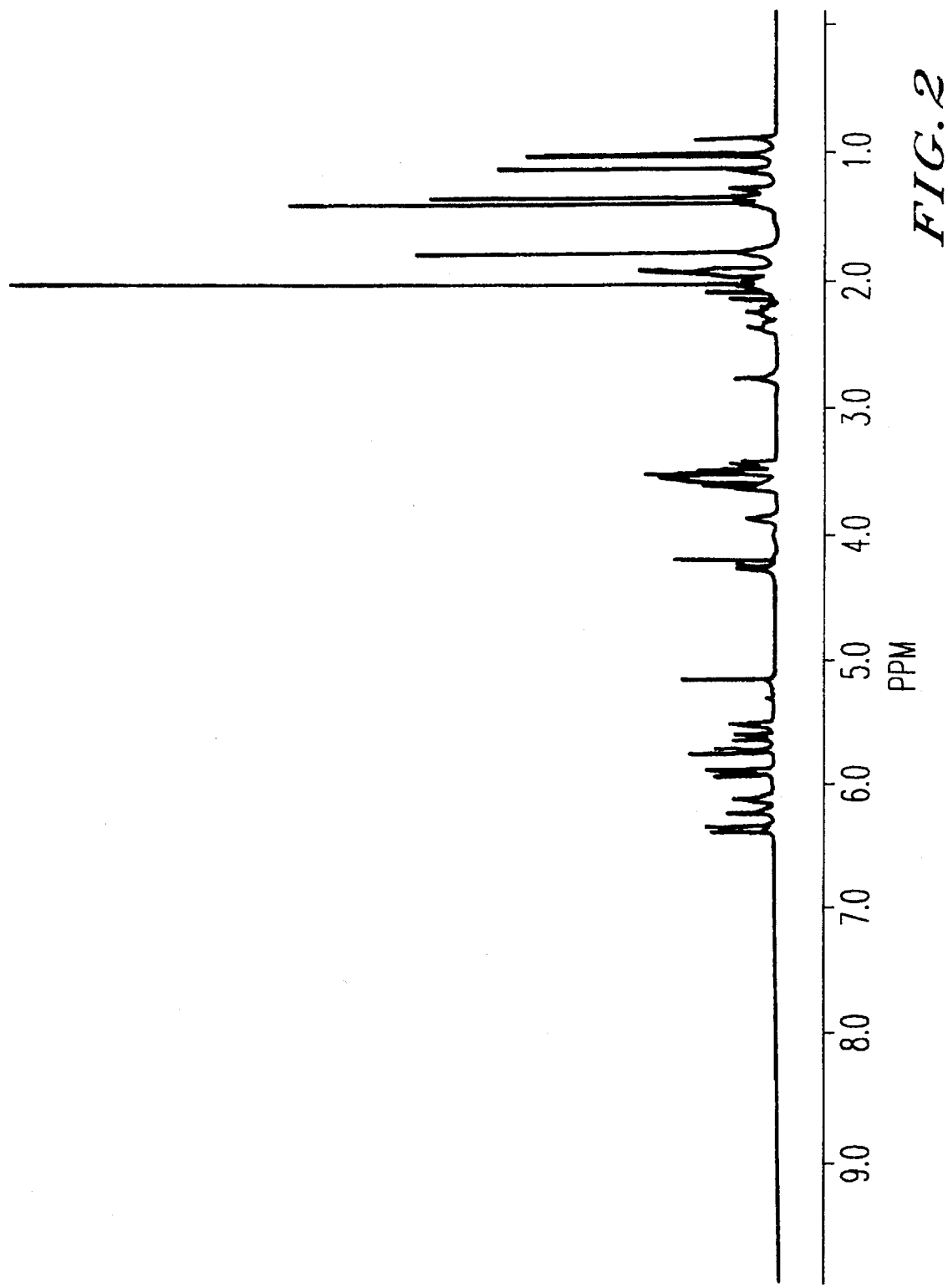
FIG. 2 is a drawing showing a $^1H$ nuclear magnetic resonance spectrum of WB2663A substance.

Chart shown in FIG. 2

$\delta_H$: 6.37(1H, d, J=16 Hz), 6.24 (1H, m), 6.13(1H, d, J=9 Hz, exchangeable), 5.91(1H, dd, J=11.5, 8 Hz), 5.73(1H, dd, J=11.5, 1 Hz), 5.64(1H, dd, J=16, 7 Hz), 5.53(1H, m), 5.16 (1H, s, exchangeable), 4.27(1H, dd, J=9.5, 7 Hz), 4.20(1H, s, exchangeable), 3.88(1H, m), 3.63(1H, m), 3.59(1H, d, J=11 Hz), 3.51(1H, d, J=11 Hz), 3.50(1H, m), 3.44(1H, dd, J:9.5, 7.5 Hz), 2.76(1H, d, J:7.5 Hz, exchangeable), 2.35(1H, m), 2.22(1H, m), 2.05(1H, d, J=14 Hz), 2.01(3H, s), 1.92(1H, d, J:14 Hz), 1.91(2H, m), 1.78 (3H, br s), 1.75(1H, m), 1.38(3H, s), 1.34(3H, d, J=6.5 Hz), 1.11(3H, d, J=6.5 Hz), 1.00(3H, d, J=7.5 Hz).

(13) Molecular formula and molecular weight $C_{27}H_{42}ClNO_8$

FAB-MS m/z 566 (M+Na)$^+$

(14) Acidity/basicity classification of substance

Neutral substance

(15) Ultraviolet absorption spectrum $\lambda$acetonitrile nm($\epsilon$): 234 (38,000) max Physicochemical properties of WB2663B substance (1) Color and form of substance White powder (2) Melting point

65°–70° C.

(3) Specific rotation $[\alpha]_D^{23}$: −12° (C=0.5, $CH_2Cl_2$)

(4) Molecular formula and molecular weight

FAB-MS m/z 508 (M+H)$^+$

HRFAB-MS m/z 508.2929

(Calculated for $C_{27}H_{41}NO_8$+H: 508.2910)

(5) Solubility in solvents

Readily soluble: ethyl acetate, dichloromethane, acetonitrile, chloroform

Hardly soluble: water

Insoluble: hexane (6) Color reaction

Positive: iodine vapor reaction, cerium sulfate reaction, potassium permanganate reaction Negative: ferric chloride reaction, ninhydrin reaction, Ehrlich reaction (7) Thin-layer chromatography

| Stationary Phase | Developing solvent | Rf value |
|---|---|---|
| Silica Gel 60 $F_{254}$ (product of E. Merck Co.) | dichloromethane:acetone (2:3) | 0.50 |
| RP-18W $F_{254}S$ (product of E. Merck Co.) | acetonitrile:water (60:40) | 0.18 |

(8) High performance liquid chromatography

Column: YMC AM-303 [S-5, 120A, ODS, 4.6 mmID×250 mm; product of Yamamura Chemical Laboratories, Ltd.]

Detection: 210 nm

Developing solvent: 40% aqueous acetonitrile

Flow rate: 1 ml/min

Retention time (RT): 12.2 min (9) $^{13}$C nuclear magnetic resonance spectrum (100 MHz, $CD_2Cl_2$)

Figure 3:
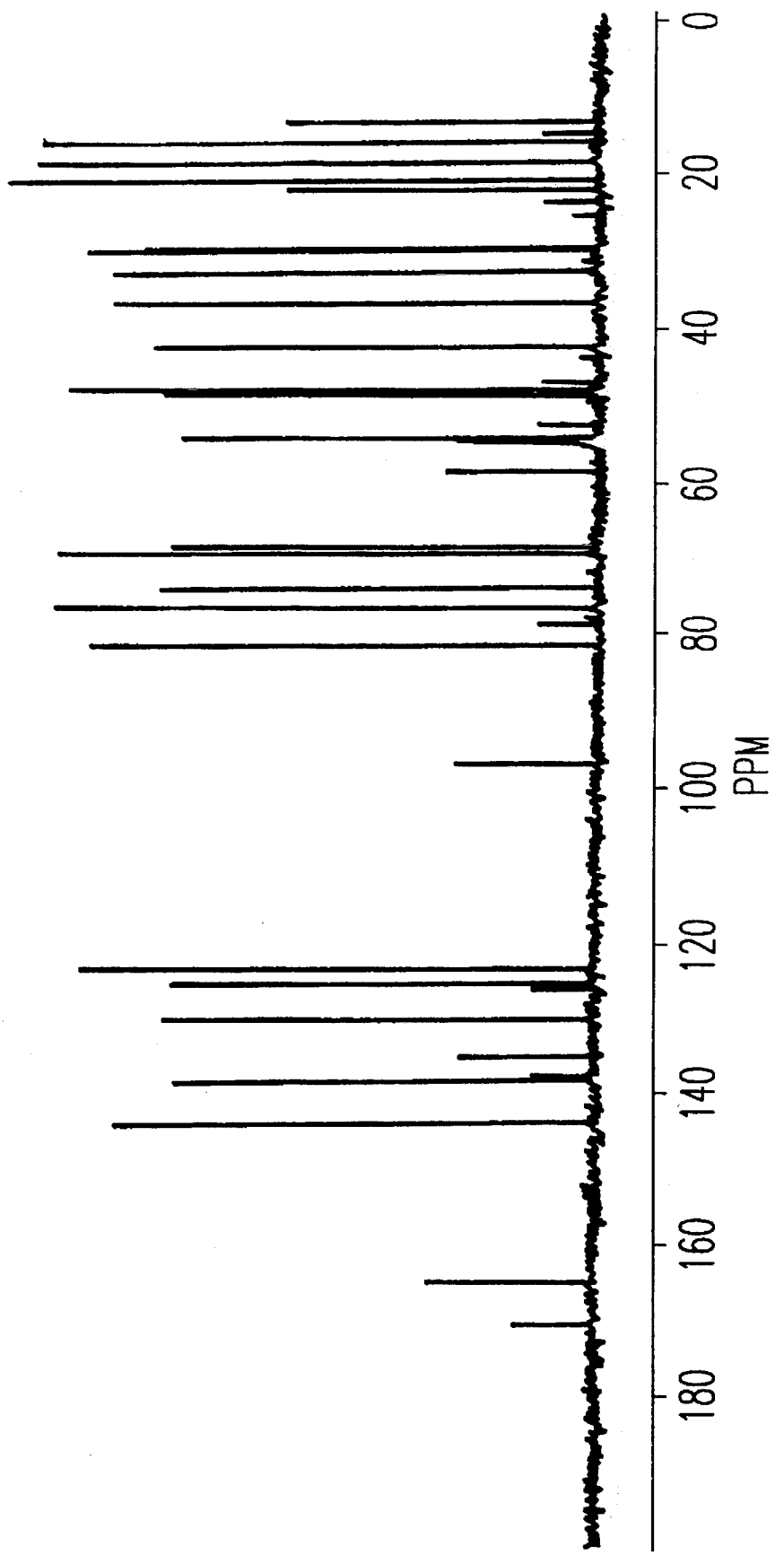
FIG. 3 is a drawing showing a $^{13}C$ nuclear magnetic resonance spectrum of WB2663B substance.

Chart shown in FIG. 3

$\delta_c$: 170.7(s), 165.0(s), 143.9(d), 138.3(d), 134.9(s), 129.8(d), 124.8(d), 122.9(d), 96.7(s), 81.2(d), 76.3(d), 73.8(d), 68.9(d), 68.2(d), 58.2(s), 48.1(t), 47.5(d), 41.9(t), 36.3(t), 32.4(t), 29.6(d), 29.2(q), 21.4(q), 20.2(q), 18.0(q), 15.3(q), 12.8(q).

(10) $^1$H nuclear magnetic resonance spectrum (400 MHz, $CD_2Cl_2$)

Figure 4:
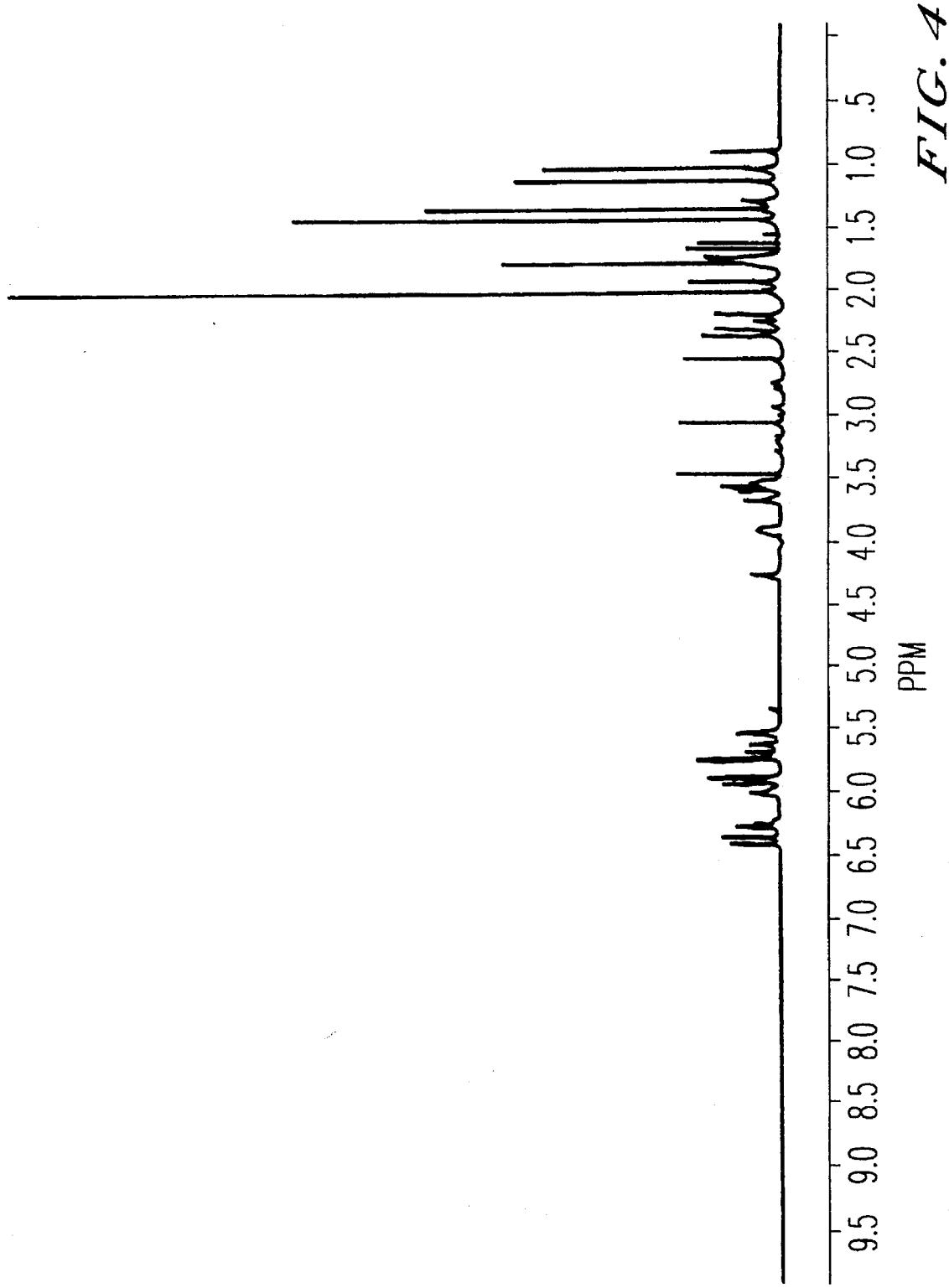
FIG. 4 is a drawing showing a $^1H$ nuclear magnetic resonance spectrum of WB2663B substance.

Chart shown in FIG. 4

The significant signals were as follows:

$\delta_H$: 6.38(1H, d, J=16 Hz), 6.26(1H, m), 6.00(1H, d, J=9 Hz, exchangeable), 5.89(1H, dd, J=11.5 and 8 Hz), 5.72(1H, dd, J=11.5 and 1 Hz), 5.66(1H, dd, J=16 and 7 Hz), 5.53(1H, m), 4.26(1H, m), 3.89(1H, m), 3.68–3.50(3H, m), 3.46(1H, s, exchangeable), 3.05(1H, d, J=4.5 Hz), 2.54(1H, d, J=4.5 Hz), 2.36(1H, m), 2.32(1H, d, J=14 Hz), 2.23(1H, m), 2.01(3H, s), 1.92(2H, m), 1.78(3H, br s), 1.75(1H, m), 1.64(1H, d, J=14 Hz), 1.42(3H, s), 1.33(3H, d, J=6.5 Hz), 1.11(3H, d, J=6.5 Hz), 1.01(3H, d, J=7.5 Hz).

(11) Acidity/basicity classification of substance

Neutral substance

(12) Ultraviolet absorption spectrum $\lambda$acetonitrile nm($\epsilon$): 235 (30,500) max

(13) Infrared absorption spectrum

KBr: 3400, 2980, 2930, 1735, 1665, 1640, 1630, 1530, $\nu$max 1370, 1250, 1050, 970 cm$^{-1}$ Physicochemical properties of WB2663C substance (1) Color and form of substance White powder (2) Melting point

86°–91° C.

(3) Specific rotation $[\alpha]_D^{23}$: −9° (C=0.5, $CH_2Cl_2$)

(4) Molecular formula and molecular weight

FAB-MS m/z 524 (M+H)$^+$

HRFAB-MS m/z 524.2849

(Calculated for $C_{27}H_{41}NO_9$+H: 524.2860)

(5) Solubility in solvents

Readily soluble: acetonitrile, chloroform, dichloromethane

Hardly soluble: water

Insoluble: n-hexane, cyclohexane, carbon tetrachloride (6) Color reaction

Positive: cerium sulfate reaction, potassium permanganate reaction

Weakly positive: iodine vapor reaction

Negative: ferric chloride reaction, ninhydrin reaction, Ehrlich reaction (7) Thin-layer chromatography

| Stationary phase | Developing solvent | Rf value |
|---|---|---|
| Silica Gel 60 $F_{254}$ (product of E. Merck Co.) | acetone | 0.44 |
| | dichloromethane:acetone (2:3) | 0.08 |
| RP-18 $WF_{254}S$ (product of E. Merck Co.) | acetonitrile:water (60:40) | 0.81 |

(8) High performance liquid chromatography

Column: YMC AM-303 [S-5,120A, ODS, 4.6 mmID×250 mm; product of Yamamura Chemical Laboratories, Ltd.]

Detection: 210 nm

Developing solvent: 40% aqueous acetonitrile

Flow rate: 1 ml/min

Retention time (RT): 8.8 min (9) $^{13}C$ nuclear magnetic resonance spectrum (100 MHz, $CD_2Cl_2$)

Figure 5:
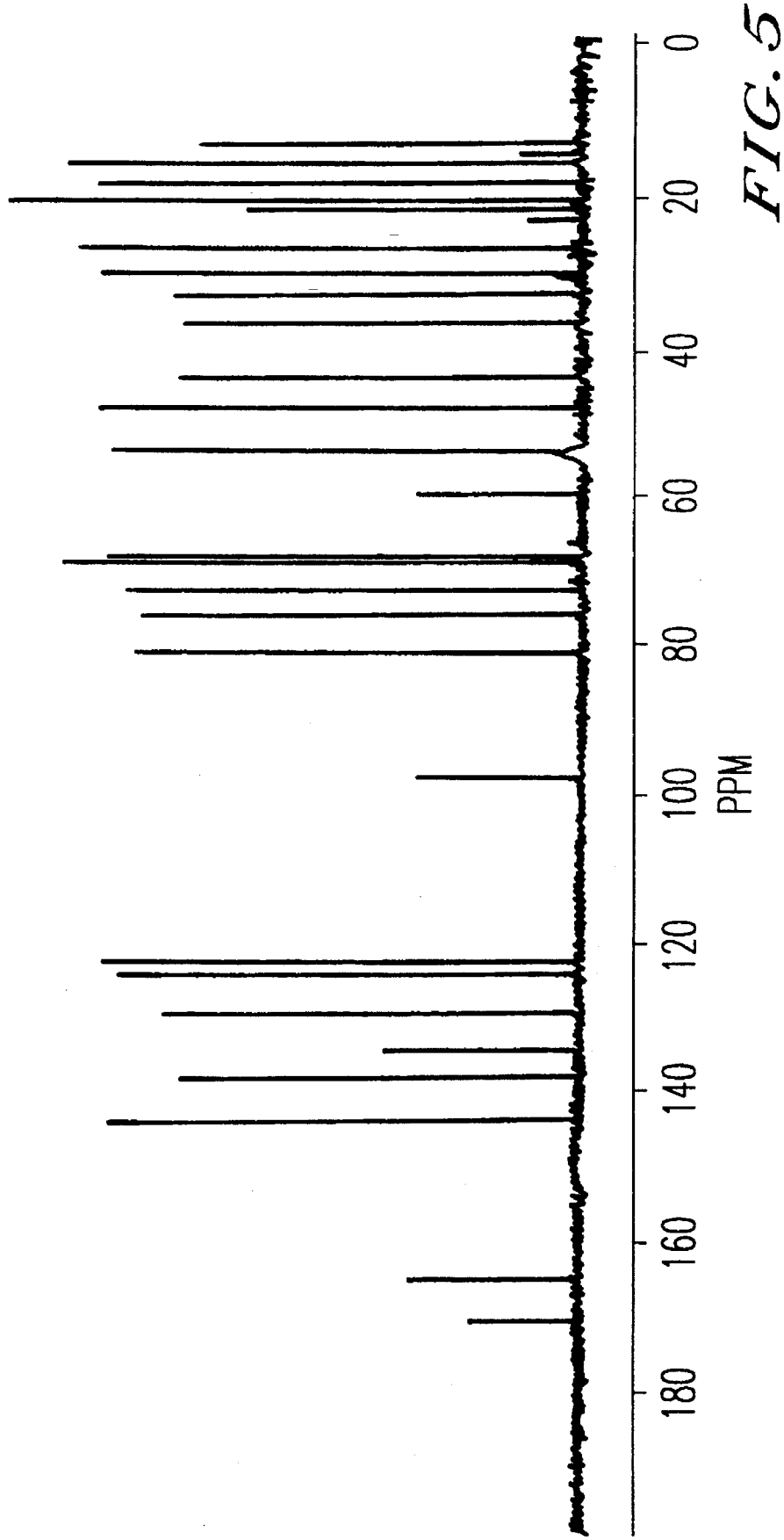
FIG. 5 is a drawing showing a $^{13}C$ nuclear magnetic resonance spectrum of WB2663C substance.

Chart shown in FIG. 5

$\delta_c$: 170.7(s), 165.2(s), 144.0(d), 138.4(d), 134.9(s), 129.9(d), 124.6(d), 122.8(d), 97.8(s), 81.3(d), 76.3(d), 73.0(d), 69.3(d), 69.0(d), 68.3(d), 59.9(s), 47.5(d), 43.5(t), 36.2(t), 32.5(t), 29.6(d), 26.5(q), 21.4(q), 20.2(q), 18.0(q), 15.3(q), 12.8(q).

(10) $^1H$ nuclear magnetic resonance spectrum (400 MHz, $CD_2Cl_2$)

Figure 6:
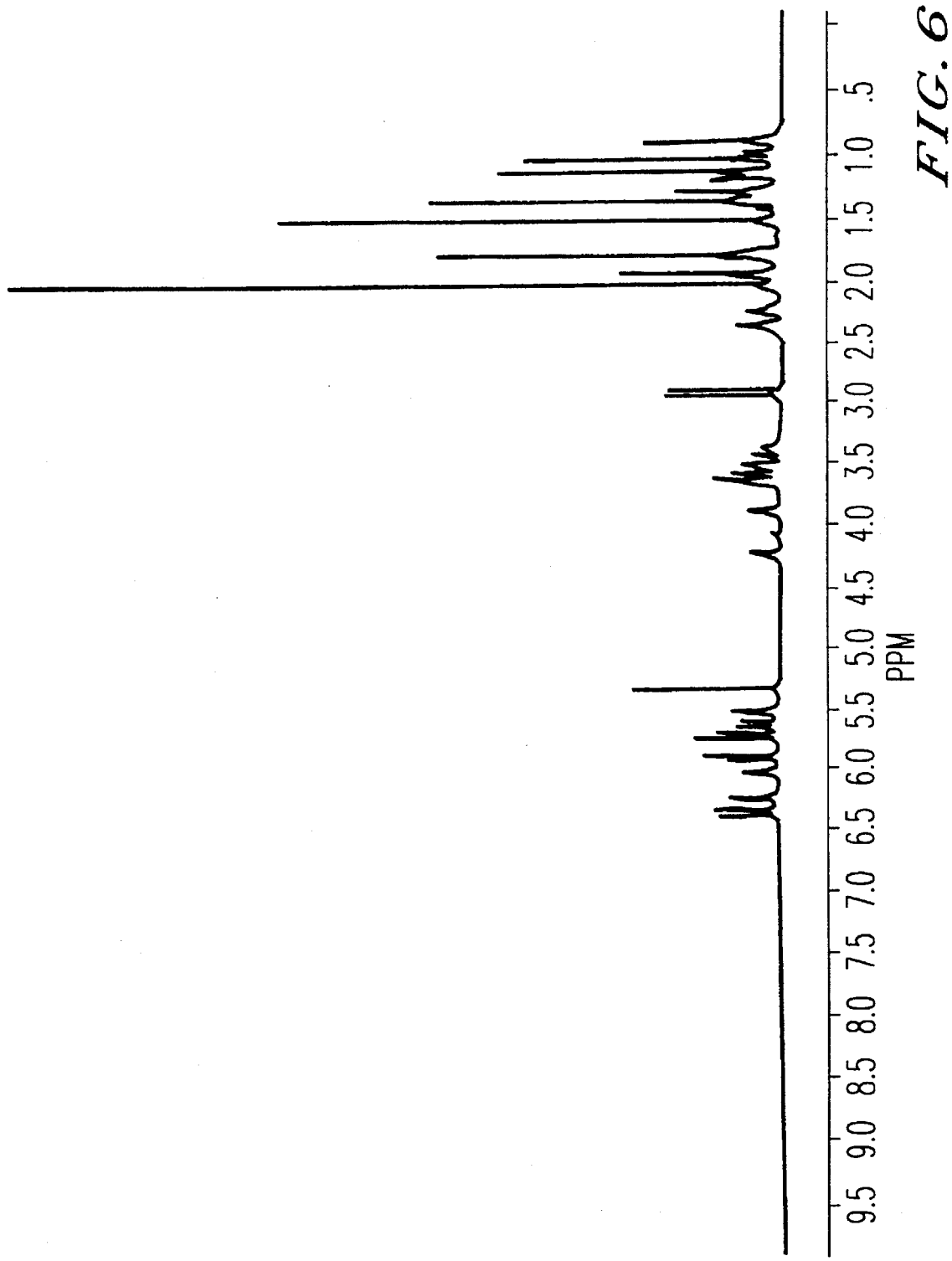
FIG. 6 is a drawing showing a $^1H$ nuclear magnetic resonance spectrum of WB2663C substance.

Chart shown in FIG. 6

The significant signals were as follows:

$\delta_H$: 6.37(1H, d, J=16 Hz), 6.25(1H, m), 6.04(1H, d, J=9 Hz, exchangeable), 5.90(1H, dd, J=11.5 and 8 Hz), 5.72(1H, dd, J=11.5 and 1 Hz), 5.64(1H, dd, J=16 and 7 Hz), 5.52(1H, m), 5.33(1H, s, exchangeable), 4.24(1H, m), 3.89(1H, m), 3.68–3.49(4H, m), 2.94(1H, d, J=5 Hz), 2.90(1H, d, J=5 Hz), 2.35(1H, m). 2.23(1H, m), 2.01(3H, s), 1.92(2H, m), 1.78(3H, br s), 1.75(1H, m), 1.50(3H, s), 1.34(3H, d, J=6.5 Hz), 1.11(3H, d, J=6.5 Hz), 1.01(3H, d, J=7.5 Hz).

(11) Acidity/basicity classification of substance

Neutral substance

(12) Ultraviolet absorption spectrum $\lambda$acetonitrile nm($\epsilon$): 235 (29,000) max

(13) Infrared absorption spectrum

KBr: 3400, 2980, 2930, 1735, 1665, 1630, 1520, 1370, $\nu$max 1250, 1115, 1050, 970 $cm^{-1}$ The WB2663 substances according to the present invention are produced by, for example, bacterial strain No. 2663 which the present inventors newly separated from soil samples collected in Mie Prefecture.

Research into the taxonomy of the bacterium of interest was mainly conducted according to the method described in Bergey's Manual of Systematic Bacteriology (Volume 1). The bacteriological properties of the bacteria of interest are given below.

(1) Morphological characteristics

The bacteria of interest were grown on a nutrient agar culture medium at 30° C. for 24 hours, after which the morphology thereof was observed under a light microscope. The results are listed in Table 1 below.

TABLE 1

| Morphological characteristics of strain No. 2663 | |
|---|---|
| Gram stain | negative |
| Color tone of colony | grayish yellow |
| Cell morphology | bacillus |
| Cell size | 0.8–1.0 × 1.5–3.0 μm |
| Mobility | positive |
| Sporulation | negative |

In other words, the bacterium of interest is gram-negative, mobile bacilli. The cells are 0.8–1.0×1.5–3.0 μm in size. The bacterium of interest formed a pink soluble pigment on a glucose-peptone agar medium.

(2) Physiological characteristics

The physiological characteristics of the bacterium of interest are listed in Table 2 below.

TABLE 2

| Physiological properties of strain No. 2663 | |
|---|---|
| Growth temperature range | 13–35° C. |
| Growth in air | positive |
| Growth on MacConkey's agar medium | positive |
| Catalase | positive |
| Oxidase | positive |
| O-F test | oxidation |
| Utilization of citric acid | positive |
| Reduction of nitrate | negative |
| Indole production | negative |
| $H_2S$ production (SIM) | negative |
| Esculin hydrolysis | negative |
| Starch hydrolysis | negative |
| ONPG test | negative |
| DNase | negative |
| Tween 80 hydrolysis | positive |
| Gelatin hydrolysis | positive |
| Caseine hydrolysis | positive |
| Lysine decarboxylase | positive (weak) |
| Arginine dihydrolase | negative |
| Ornithine decarboxylase | negative |
| Acid production from sugars | |
| D-glucose | positive |
| D-xylose | negative |
| D-fructose | positive |
| D-mannitol | positive |
| Maltose | negative |
| Sucrose | positive |
| Lactose | positive |
| Salicin | negative |
| Utilization of sugars and organic acids | |
| D-glucose | positive |
| D-arabinose | negative |
| D-mannose | positive |
| D-mannitol | positive |
| N-acetyl-D-glucosamine | positive |
| Maltose | negative |
| Gluconic acid | positive |
| Capric acid | positive |
| Adipic acid | positive |
| Malic acid | positive |
| Citric acid | positive |
| Phenyl acetate | positive |

As is clear from Table 2, the temperature range for growth of the bacterium of interest was from 13° C. to 35° C. The bacterium was positive for oxidase and catalase, and was oxidative in the O-F test. The bacterium of interest was positive for the decomposition of gelatin, caseine and Tween 80. It was negative for the decomposition of starch, but positive for lysine carboxylase. It produced acids from D-glucose, D-fructose, D-mannitol, sucrose and lactose. It utilized D-glucose, D-mannose and D-mannitol, but did not utilize L-arabinose and maltose.

(3) Identification

As a result of examining the above mentioned characteristics against Bergey's Manual of Systematic Bacteriology (Volume 1), strain No. 2663 was assumed to belong to Pseudomonas. The bacterial strain of interest was thus identified as Pseudomonas sp. No. 2663.

Strain No. 2663 is deposited at National Institute of Bioscience and Human-Technology Agency of Industrial Science and Technology, Ministry of International Trade and Industry in Japan (Deposit No.: FERM BP-3421, Deposit date: May 21, 1991).

It should be understood that the production of the present substances is not limited only to the use of the specific microorganism which is described in the present specification and provided solely for explanation. The present invention encompasses the use of all mutants capable of producing the substances of interest, including artificially mutated strains obtained from the listed microorganism using methods of mutagenesis such as X-ray irradiation, ultraviolet irradiation, N-methyl-N'-nitro-N-nitrosoguanidine, 2-aminopurine, etc., as well as naturally mutated strains.

The substances according to the present invention may be produced by inoculating said substance-producing bacterium belonging to the genus Pseudomonas (e.g. Pseudonomas sp. No. 2663) into a nutrient culture medium containing carbon and nitrogen sources which can be utilized by the bacterium, and culturing it under aerobic conditions (e.g. shake culturing, aeration culturing while stirring, etc.).

The carbon sources preferred for use include glucose, sucrose, starch, modified starch, fructose, glycerin and other carbohydrates.

The nitrogen sources preferred for use include oatmeal, yeast extract, peptone, gluten meal, cottonseed flour, cottonseed oil, soybean flour, corn steep liquor, dried yeast, wheat germ, peanut flour, chicken bone and meal meat, etc., but inorganic and organic nitrogen sources such as ammonium salts (e.g. ammonium nitrate, ammonium sulfate, ammonium phosphate, etc.), urea, amino acids, etc. may be used with advantages.

These carbon sources and nitrogen sources may be used together with advantages, and there is no particular need to use them in their pure form. This is because impure forms sometimes contain growth factors and trace elements, which can be advantageous.

If necessary, inorganic salts such as, for example, the following may be added to the culture medium: sodium carbonate, potassium carbonate, sodium phosphate, potassium phosphate, sodium chloride, potassium chloride, sodium iodide, potassium iodide, magnesium salts, copper salts, cobalt salts, etc.

Particularly, if the medium is strongly effervescent, liquid paraffin, animal oils, vegetable oils, mineral oils, silicon, etc. may be added when necessary.

For industrial production of the desired substance in large amounts, aeration culturing while stirring is preferred, as in the case of other fermentates. For production in small amounts, shake culturing using a flask is suitable.

In addition, if culturing is effected in a large tank, it is preferable first to inoculate seed producing cells in a relatively small amount of the medium for cultivation, and then transfer the culture to a large production tank for production culturing, in order to prevent delayed growth of the cells during the process for the production of the substance of interest. In such cases, the respective compositions of both the medium used for pre-culturing and the medium used for production culturing may be identical or modified if necessary.

The culturing is preferably effected under aerated conditions while stirring, and known methods, for example, stirring with a propeller or another device, rotation or shaking of a fermenter, pump processing, blowing with air, etc., are suitable for use. The air used for aeration is sterilized.

The culturing temperature may be appropriately varied within a range in which the substance-producing bacteria can produce the substance, but culturing is normally effect at 1°–40° C., and preferably 14°–36° C. The culturing time differs depending on the conditions and the amount of culturing to be done, but is normally from about 1 day to 1 week.

After completion of fermentation, the desired substance of interest is collected from the culture. That is, the cells are extracted directly with water and/or an organic solvent, or the cells are crushed either mechanically or by a known method such as using ultrasonic waves, etc. after which they are extracted using water and/or an organic solvent, and then collected and purified according to a conventional method. In the case of a culture solution, the substance may be directly collected and purified using a conventional method.

The methods for collection and purification include conventional methods such as solvent extraction using, for example, water, an organic solvent or mixed solvents thereof; chromatography; recrystallization from a single solvent or a mixed solvent, etc., and these may be appropriately employed either alone or in combination.

The isolation and purification of the substance of interest is effected by the appropriate employment of the known methods mentioned above, but each of the 3 effective components may be isolated and purified in the following manner, for example. First, the organic solvent (e.g. ethyl acetate) extract from the culture is passed through a silica gel column, a developing solvent is charged, further column treatment is effected if necessary, and the mixture is subjected to treatment with various developing solvents to obtain fractions rich in WB2663A substance, fractions rich in WB2663B substance and fractions rich in WB2663C substance, respectively. These fractions are then further purified. For example, each of the fractions is extracted with a single or mixed solvent, and the extracts are evaporated or distilled for concentration. The concentrated residues are subjected to chromatography or recrystallization, and lyophilized if necessary, to obtain the further purified components.

A medicinal composition according to the present invention is prepared into a solid, semi-solid or liquid form as a preparation for oral administration or parenteral administration such as an external application, etc., by using 1, 2 or more of the substances of interest and/or their salts as the effective components, and adding a commonly used inorganic or organic carrier thereto.

The preparations for oral administration include tablets, pills, granules, soft/hard capsules, powders, fine granules, dusting powders, emulsions, suspensions, syrups, pellets, elixirs, etc. The preparations for parenteral administration include injections, drips, infusions, pastes, lotions, tonics, sprays, suspensions, oils, emulsions, suppositories, etc. The preparation of an effective component according to the present invention may be done following a conventional procedure, with the appropriate use of a surfactant, excipient, coloring agent, perfume, preservative, stabilizer, buffer, suspending agent, isotonizing agent or other conventionally used auxiliary.

The dosage of a medicinal composition according to the present invention differs depending on its kind, the type of disease for treatment or prevention, the method of administration, the age and symptoms of the patient, and the length of the treatment period. However, the administration of the effective components (substances of interest) per day for an adult is in the range of 0.01–1000 mg/kg, and preferably 0.1–100 mg/kg in the case of intravenous injection; 0.01–1000 mg/kg, and preferably 0.1–100 mg/kg in the case of intramuscular injection; and 0.5–2000 mg/kg, and preferably 1–1000 mg/kg in the case of oral administration.

A more detailed explanation of the present invention is provided below, with reference to the examples.

EXAMPLE 1

(1) Culturing of strain No. 2663

A medium composed of 1% polypeptone (product of Nihon Seiyaku, Ltd.), 0.5% yeast extract (product of Nihon Seiyaku, Ltd.) and 0.5% NaCl was poured in portions of 160 ml each into 500 ml Erlenmeyer flasks, and sterilized at 120° C. for 30 minutes. A slant culture of Pseudomonas sp. No. 2663 (FERM BP-3421) was transplanted thereto one loopful, and culturing was effected at 30° C. for 24 hours in a rotary shaker (220 rotations/min), to prepare seed culture. Separately, 20 l of a medium at pH 7.0 containing 1% modified starch, 1% glycerin, 0.5% glucose, 1% defatted soybean meal, 0.5% corn steep liquor, 0.2% $(NH_4)_2SO_4$, 0.006% $MgSO_4 \cdot 7H_2O$, 0.2% $CaCO_3$, 0.05% adecanol (LG-109, Asahi Denka Kogyo K. K.) and 0.05% silicon (KM-70, Shin-Etsu Chemical Co., Ltd.)was poured into each of 30 liter jar fermenters and sterilized at 120° C. for 30 minutes, and then 480 ml of the above-mentioned seed culture was added thereto and cultured at 25° C. for 2 days, at a aeration volume of 20 l/min, an internal pressure of 1 kg/cm$^2$, and 200 rotations/min.

(2) Isolation/purification of the substances produced by strain No. 2663

After culturing was completed, 400 l of the culture gathered from twenty 30-liter jar fermenters was adjusted to pH 7.0, extracted twice with 1.5-fold volume (600 l) of ethyl acetate, and the extracts were combined for concentration under reduced pressure. To the concentrate was added anhydrous sodium sulfate for dehydration, after which 1.7 l of Silica Gel 60 (70–230 mesh, product of E. Merck Co.) was added thereto, followed by drying under reduced pressure. The resulting powder was placed on a 4 liter silicagel column (same as above) which had been prefilled with n-hexane, and chromatography was effected. That is, successive elutions were made with 17 l of n-hexane, 17 l of n-hexane:ethyl acetate (3:1), 17 l of n-hexane:ethyl acetate (1:1), 17 l of ethyl acetate and 17 l of ethyl acetate:acetone (1:1), upon which WB2663A substance was eluted in the n-hexane:ethyl acetate (1:1) fraction, and WB2663B and WB2663C substances were eluted in the ethyl acetate fraction.

First, the method of purification of WB2663A substance will be described below. The n-hexane:ethyl acetate (1:1) fraction was concentrated under reduced pressure, and the resulting oily substance (21 g) was combined with 50 ml of silicagel (same as above) and dried under reduced pressure. The resulting powder was placed on a 450 ml silicagel column (same as above) which had been pre-filled with n-hexane, and chromatography was effected. That is, successive elutions were made with 2.5 l of n-hexane, 2.5 l of n-hexane:acetone (8:1), 2.5 l of n-hexane:acetone (6:1), 2.5 l of n-hexane:acetone (4:1), 2.5 l of n-hexane:acetone (2:1) and 2.5 l of n-hexane:acetone (1:1), upon which activity was observed in the n-hexane:acetone (4:1) and (2:1) fractions. The active fractions were combined and concentrated under reduced pressure, the resulting oily substance (8 g) was dissolved in 700 ml of a 10% aqueous solution of acetonitrile, and placed in a 200 ml ODS gel (YMC ODS-AM 120-S50, product of Yamamura Kagaku Co.) column which had been pre-filled with water for reverse phase chromatography. Upon successive elutions of the column with 600 ml each of 10%, 20%, 30% and 40% aqueous solutions of acetonitrile, activity was observed in the fraction of the 40% aqueous solution of acetonitrile. The active fraction was concentrated under reduced pressure and the acetonitrile removed, after which extraction was made twice with equal volumes of ethyl acetate and the extracts were combined and concentrated and dried to solidity. The concentrated residue was dissolved in a small amount of dichloromethane, and n-hexane was added thereto to obtain 512 mg of colorless needle-shaped crystals of WB2663A substance.

Next, an explanation will be given regarding the method of purification of WB2663B substance. The previously mentioned ethyl acetate fraction was concentrated under reduced pressure, and the resulting oily substance (62.9 g) was dissolved in 1.1 l of n-hexane:chloroform (4:7), and placed in 1.2 l of silicagel (same as above) which had been pre-filled with n-hexane:chloroform (1:1). Upon successive elutions of the column with 3.6 l each of chloroform:acetone mixtures (1:0, 100:1, 50:1, 25:1 and 10:1), activity was observed in the chloroform:acetone (100:1) and (50:1) fractions. The WB2663C substance, described later, was eluted in the chloroform:acetone (25:1) fraction. The active fractions were combined and concentrated under reduced pressure, and the resulting oily substance (7.2 g) was dissolved in 2 l of a 20% aqueous solution of acetonitrile and placed in a 200 ml pre-filled ODS gel (same as above) column which had been prepacked with a 20% aqueous solution of acetonitrile for reverse phase chromatography. Upon successive elutions of the column with 600 ml each of 25% and 27% aqueous solutions of acetonitrile, activity was observed in the fraction of the 27% aqueous solution of acetonitrile. The active fraction was concentrated under reduced pressure and therefrom the acetonitrile removed, after which extraction was made twice with equal volumes of ethyl acetate and the extracts were combined and concentrated under reduced pressure to obtain 819 mg of white powder of WB2663B substance.

Next, an explanation will be given regarding the method of purification of WB2663C substance. The previously mentioned chloroform:acetone (25:1) fraction was concentrated under reduced pressure, and the resulting oily substance was dissolved in 300 ml of chloroform:n-hexane (1:1), and placed in a 100 ml silica gel (same as above) column which had been pre-filled with n-hexane:acetone (10:1). Upon elution of the column with 300 ml each of n-hexane:acetone mixtures (5:1, 4:1, 7:2, 3:1, 2:1, 1:1 and 0:1), activity was observed in the n-hexane:acetone (1:1) and acetone fractions. Both of the active fractions were combined and concentrated under reduced pressure, and the resulting oily substance was dissolved in 125 ml of a 20% aqueous solution of acetonitrile and placed in a 200 ml YMC gel (same as above) column which had been pre-filled with a 10% aqueous solution of acetonitrile. Upon elution of the column with 500 ml each of 24% and 26% aqueous solutions of acetonitrile, activity was observed in the fraction of the 26% aqueous solution of acetonitrile. The active fraction was concentrated under reduced pressure and the acetonitrile removed therefrom, after which extraction was made twice with equal volumes of ethyl acetate, the extracts were combined and concentrated to dryness under reduced pressure, the residue was dissolved in a small amount of dichloromethane, and then n-hexane was added thereto to obtain 70 mg of white powder of WB2663C substance.

EXAMPLE 2

(In vitro human tumor cell growth inhibition by the substance of interest)

As described below, each of the substances of interest were investigated as to their cell toxicities against A549 human pulmonary adenocarcinoma, MCF-7 human mammary adenocarcinoma, SW480 human colon adenocarcinoma, HCT116 human colon adenocarcinoma, P388 mouse leukemia cells and mouse bone marrow (BM) cells. Culturing was initiated at cell concentrations of $4 \times 10^3$/well of the human solid adenocarcinoma cells, $1 \times 10^4$/well of the mouse leukemia cells, and $1 \times 10^5$/well of the mouse bone marrow cells, and the cell toxicities were measured on the 4th day.

More specifically, the cytoxicity test was conducted in a 96-well microtitre plate, each well containing the tumor cells at the cell concentrations mentioned above in 100 µl of Dulbecco's minimum essential medium to which had been added 10% fetal calf serum, penicillin (50 units/ml) and streptomycin (50 µg/ml). The cells were incubated at 37° C.

for 4 days, and a colorimetric MTT (3-(4,5-dimethylthiazole- 2-il)-2,5-diphenyltetrazoliumbromide, product of Sigma Co.) assay was made according to the method described by Mosmann in J. Immunol. Methods, 65, 55–63, 1983.

First, MTT was dissolved in a phosphate buffer solution (PBS) to a concentration of 5 mg/ml, and the solution was filtered and sterilized to remove the small amount of insoluble residue. After completion of culturing of the tumor cells, the MTT solution was added to all of the assay wells (10 µl per 100 µl of medium), and the plate was further incubated at 37° C. for 4 hours. Acidic isopropanol (100 µl of 0.04 N HCl in isopropanol) was added to all of the wells, and mixing was effected to dissolve the dark blue crystals. After all of the crystals dissolved, the plate was subjected to a dual wavelength photometer (Model MIP-22: Corona Denki Co., Inc., Katsuta-shi, Japan) at 550 nm and a reference wavelength of 660 nm, and read. The object compounds according to the present invention were dissolved in methanol and diluted with Dulbecco's minimum essential medium, and added to the cultures to a final concentration of 1 µg/ml or less. The results are shown in Table 3.

TABLE 3

In vitro human tumor cell growth inhibition by the substance of interest

| Cell line | $IC_{50}$ (ng/ml) WB2663A substance | WB2663B substance | WB2663C substance |
|---|---|---|---|
| MCF-7 | 0.46 | 0.91 | 0.59 |
| A549 | 0.35 | 0.66 | 0.44 |
| HCT116 | 0.22 | 0.31 | 0.34 |
| SW480 | 0.40 | 0.51 | 0.53 |
| P388 | 0.82 | 1.69 | 0.48 |
| BM | 2.03 | 5.01 | 1.91 |

MCF-7: human mammary adenocarcinoma
A549: human pulmonary adenocarcinoma
HCT116: human colon adenocarcinoma
SW480: human colon adenocarcinoma
P388: mouse leukemia cells
BM: mouse bone marrow cells As is clear from the results in Table 3, all 3 components of the substance of interest exhibited a strong cytoxicity against all of the human solid cancer, as well as cytoxicity, though weaker, against mouse leukemia cells (WB2663A substance and WB2663B substance) and mouse bone marrow cells.

EXAMPLE 3

(Life lengthening test with P388 mouse leukemia cells)

P388 mouse leukemia cells were intraperitoneally transplanted to $BDF_1$ mice (female, 7 weeks old) at $1\times10^6$ cells/mouse ($5\times10^6$ cells/ml×0.2 ml/mouse), and from the following day, WB2663A substance, WB2663B substance and WB2663C substance dissolved in 10% HCO-60 [polyoxy ethylated (60 mole) hydrogenated castor oil in saline (product of Nikko Co.)] (pH 7.0) were each intraperitoneally administered once a day for 4 days (d1, d2, d3, d4), at doses of 0.2 ml/mouse. To the control mice, 10% HCO-60 (same as above) was administered. The numbers d1–d4 indicate the data from day 1 to day 4, respectively.

The results are shown in Table 4 below. The antitumor activity was expressed as the number of animals died/number of animals treated (D/T), the body weight change during the treatment period (d4–d1), the median survival time (MST) of the group, and T/C% (100×treated group/control group) of the median survival time.

TABLE 4

Life lengthening effect of the substance of interest

| Dose (mg/kg) | D/T | Body weight change d4-d1 (g) | MST (days) | T/C (g) |
|---|---|---|---|---|
| WB2663A substance | | | | |
| Control | 0/5 | 0.4 | 10 | 100 |
| 0.1 | 0/5 | 0.1 | 10 | 100 |
| 0.18 | | | | |
| 0.32 | 0/5 | 0.3 | 11 | 110 |
| 1.0 | 0/5 | -0.3 | 16 | 160 |
| 3.2 | 1/5 | -1.7 | 14.5 | 145 |
| WB2663B substance | | | | |
| Control | 0/5 | 0.4 | 11 | 100 |
| 0.018 | 0/5 | 0 | 13 | 118 |
| 0.032 | 0/5 | -0.4 | 12 | 109 |
| 0.056 | 0/5 | -0.6 | 15 | 136 |
| 0.1 | 0/5 | -1.6 | 16 | 145 |
| 0.18 | 2/5 | -2.0 | 15 | 136 |
| WB2663C substance | | | | |
| Control | 0/5 | 0.4 | 11 | 100 |
| 0.0032 | 0/5 | 0.4 | 12 | 109 |
| 0.01 | 0/5 | -0.3 | 13 | 118 |
| 0.032 | 0/5 | -1.6 | 14 | 127 |
| 0.056 | | | | |
| 0.1 | 4/5 | -2.8 | 17 | 155 |

As is clear from the results in Table 4, a life lengthening effect was exhibited towards P388 mouse leukemia tumor-bearing mice at 1 mg/kg and 3.2 mg/kg of WB2663A substance, 0.056 mg/kg, 0.1 mg/kg and 0.18 mg/kg of WB2663B substance, and 0.032 mg/kg of WB2663C substance.

EXAMPLE 4

(Antitumor effect against A549 human pulmonary adenocarcinoma cells)

A549 human pulmonary adenocarcinoma cells which had been subcultured under the skin of nude mice (female, 7 weeks old) were cut into slices 1 mm square and implanted one under the renicapsule of $BDF_1$ mice (female, 7 weeks old). On the following day (first day), the fifth day and the ninth day, WB2663A substance or WB2663B substance which had been dissolved in 10% HCO-60 [polyoxyethlated (60 mole) hydrogenated castor oil in saline (produce of Nikko Co.)] (pH 7.0) was intraperitoneally administered at dose of 0.2 ml/mouse. To the control group, 10% HCO-60 (same as above) was administered. In addition, to promote the survival of the tumors, 32 mg/kg of immunosuppressant agent FK506 (Fujisawa Pharmaceutical Co., Ltd.) suspended in physiological saline was subcutaneously administered at dose (32 mg/kg) of 0.2 ml/mouse on the 1st, 2nd, 5th, 7th, 9th and 12th days. Groups of 8 mice each were used for the experiment. At 14 days after implanting, the antitumor activity was measured. The results are shown in Table 5 below (d1–d14 represent the data of the first to the 14th days, respectively). The antitumor activity was expressed as the number of animals died/number of animals treated (D/T), the body weight change during the treatment period (d14-d1), the median tumor volume of each group ($mm^3$), and the tumor volume inhibition rate (%). The tumor volume was calculated using the equation: Tumor volume ($mm^3$)= (major axis of tumor)×(minor axis of tumor)$^2$/2 while the tumor volume inhibition rate was calculated using the equation: Inhibition (%)=(median tumor volume of control group–median tumor volume of treated group)/median tumor volume of control group×100.

TABLE 5

| Drug | Dose (mg/kg) | D/T | Body weight change (g) [d14-d1] | tumor volume (mm³) | inhibition (%) |
|---|---|---|---|---|---|
| Antitumor effect of WB2663A against A549 (1) | | | | | |
| WB2663A | Control | 0/8 | 0.53 | 14.87 ± 3.75 | — |
| | 0.56 | 0/7 | −0.39 | 14.17 ± 2.63 | 5.2 |
| | 1.0 | 0/7 | −1.17 | 15.87 ± 2.31 | −6.7 |
| | 1.8 | 0/8 | −0.71 | 12.89 ± 1.86 | 13.3 |
| | 3.2 | 2/8 | −1.98 | 5.79 ± 1.15 | 61.0 |
| | 5.6 | 8/8 | — | — | — |
| Antitumor effect of WB2663B against A549 (2) | | | | | |
| WB2663B | Control | 0/8 | 1.6 | 29.16 ± 5.08 | — |
| | 0.056 | 0/7 | 1.5 | 18.53 ± 3.65 | 36.4 |
| | 0.10 | 0/8 | 1.0 | 11.36 ± 1.36** | 61.1 |
| | 0.18 | 0/8 | 0.2 | 10.74 ± 2.34** | 63.2 |
| | 0.32 | 1/8 | −0.5 | 6.63 ± 1.02** | 77.3 |
| | 0.56 | 2/8 | −1.4 | 4.85 ± 1.46** | 83.4 |
| | 1.00 | 5/7 | −2.3 | 10.58 ± 5.72 | 63.7 |

EXAMPLE 5

(Life lengthening test with. Meth A. mouse fibrosarcoma cells)

Mouse fibrosarcoma Meth A cells were intradermally transplanted to Balb/c mice (female, 7 weeks old) at 1×10⁵ cells/mouse. WB2663B substance was diluted to various medicinal concentrations using physiological saline containing 10% HCO-60, and was intravenously administered 3 times on the 8th, 11th and 14th days (d8, 11 and 14) after transplantation. To the control mice, 10% HCO-60 was administered. Groups of 10 mice each were used for the experiment.

The antitumor activity was measured on the 17th day after transplantation, and the results are shown in Table 6 below.

$$\text{Inhibition \%} = \left(1 - \frac{Tn/To}{Cn/Co}\right) \times 100$$

The antitumor activity was expressed as growth inhibition rate relative to the tumor weight:

Tn: tumor weight of treated group
Cn: tumor weight of control group
To: tumor weight of treated group at time of first administration of drug
Co: tumor weight of control group at time of first administration of drug The relative tumor weight was then calculated by:

$$\text{Tumor weight} = \frac{a \times b^2}{2}$$

a: major axis of tumor
b: minor axis of tumor

TABLE 6

Antitumor effect of WB2663B against Meth A

| Drug | Dose (mg/kg) | Body weight change (g) [day 17–8] | Tumor weight (mg) Mean ± S.E. (Inhibition %) (day 17) |
|---|---|---|---|
| WB2663B | Control | 1.8 | 1421 ± 86 |
| | 0.1 | 0.6 | 1076 ± 123**(24) |
| | 0.18 | 0.3 | 683 ± 104**(52) |
| | 0.32 | 0.6 | 737 ± 120**(48) |
| | 0.56 | −0.1 | 587 ± 94**(59) |

TABLE 6-continued

Antitumor effect of WB2663B against Meth A

| Drug | Dose (mg/kg) | Body weight change (g) [day 17–8] | Tumor weight (mg) Mean ± S.E. (Inhibition %) (day 17) |
|---|---|---|---|
| | 1.0 | −0.8 | 156 ± 58**(89) |

EXAMPLE 6

(Acute toxicity of the substance of interest)

The acute toxicity test was conducted using BDF₁ mice (female, 7 weeks old) with a single intraperitoneal administration. The results were LD$_{50}$ values of 10–5.6 mg/kg for WB2663A substance, 3.2 mg/kg for WB2663B substance, and 0.32–0.1 mg/kg for WB2663C substance.

References to the deposited microorganism under Rule 13-2
1. Pseudonomas sp. No. 2663
   a) Name and address of the depository authority in which said microorganism is deposited:
      Name: National Institute of Bioscience and Human Technology, Agency of Industrial Science and Technology, Ministry of International Trade and Industry
      Address: 1-3, Higashi 1 chome, Tsukuba-shi, Ibaraki-ken, 305, Japan
   b) Date of deposit at the depository authority shown in a) May 21, 1991
   c) Deposit No. given by the depository authority shown in a) FERM BP-3421

We claim:

1. A method for producing a WB2663 compound comprising:
   culturing Pseudomonas sp. No. 2663, FERM BP-3421, or a mutant thereof capable of producing a WB2663 compound in a medium containing assimilable sources of carbon and nitrogen and collecting a WB2663 compound having the formula $C_{27}H_{42}ClNO_8$, $C_{27}H_{41}NO_8$ or $C_{27}H_{41}NO_9$.

2. The compound WB2663A, having the properties:
   (A) Melting point
      102°–104° C.

(B) Specific rotation $[\alpha]_D^{23}$: −36° (c=0.5, $CH_2Cl_2$)

(C) Elemental analysis
Calculated for $C_{27}H_{42}ClNO_8$ (%): C, 59.60; H, 7.78; N, 2.57; Cl, 6.52
Found (%): C, 60.111; H, 8.10; N, 2.44; Cl, 6.86

(D) Infrared absorption spectrum
KBr: 3400, 2980, 2940, 1735, 1665, 1630, 1530, 1370, max
1240, 1055 $cm^{-1}$ (E) and is the same as a compound produced by Pseudomonas sp. FERM BP-3421.

3. The compound WB2663B, having the properties:

(A) Melting point
65°–70° C.

(B) Specific rotation $[\alpha]_D^{23}$: −12° (c=0.5, $CH_2Cl_2$)

(C) Molecular formula and molecular weight
HRFAB-MS m/z 508.2929
$C_{27}H_{41}NO_8$+H: 508.2910

(D) Ultraviolet absorption spectrum
235 nm (ε=30,500, in acetonitrile)

(E) and is the same as a compound produced by Pseudomonas sp. FERM BP-3421.

4. The compound WB2663C, having the properties:

(A) Melting point
86°–91° C.

(B) Specific rotation $[\alpha]_D^{23}$: −9° (c=0.5, $CH_2Cl_2$)

(C) Molecular formula and molecular weight
HRFAB-MS m/z 524.2849
$C_{27}H_{41}NO_9$+H: 524.2860

(D) Ultraviolet absorption spectrum
235 nm (ε=29,000, in acetonitrile)

(E) and is the same as a compound produced by Pseudomonas sp. FERM BP-3421.

\* \* \* \* \*